(12) United States Patent
Haugland et al.

(10) Patent No.: US 12,691,282 B2
(45) Date of Patent: Jul. 28, 2026

(54) APPARATUS AND METHOD FOR TRAINING AND ASSISTING GAIT OF A PERSON

(71) Applicant: Nordic-NeuroStim ApS, Aalborg Øst (DK)

(72) Inventors: Morten Kristian Haugland, Svenstrup J (DK); Christian Christiansen, Birkerød (DK)

(73) Assignee: Nordic-NeuroStim ApS, Aalborg Øst (DK)

( * ) Notice: Subject to any disclaimer, the term of this patent is extended or adjusted under 35 U.S.C. 154(b) by 602 days.

(21) Appl. No.: 18/248,164

(22) PCT Filed: Oct. 6, 2021

(86) PCT No.: PCT/EP2021/077490
§ 371 (c)(1),
(2) Date: Apr. 6, 2023

(87) PCT Pub. No.: WO2022/074026
PCT Pub. Date: Apr. 14, 2022

(65) Prior Publication Data
US 2023/0372708 A1 Nov. 23, 2023

(30) Foreign Application Priority Data
Oct. 9, 2020 (EP) ..................................... 20201136

(51) Int. Cl.
*A61N 1/36* (2006.01)
*A61B 5/11* (2006.01)
*A61N 1/04* (2006.01)
(52) U.S. Cl.
CPC .......... *A61N 1/36003* (2013.01); *A61B 5/112* (2013.01); *A61N 1/0452* (2013.01);
(Continued)

(58) Field of Classification Search
CPC .............. A61N 1/36003; A61N 1/0452; A61N 1/36031; A61N 1/36034; A61B 5/112;
(Continued)

(56) References Cited

U.S. PATENT DOCUMENTS

| | | | |
|---|---|---|---|
| 2008/0234782 A1 | 9/2008 | Haugland et al. | |
| 2011/0178572 A1* | 7/2011 | Czyrny | A61N 1/36031 |
| | | | 607/46 |

(Continued)

OTHER PUBLICATIONS

International Search Report and Written Opinion mailed Jan. 14, 2022, issued in corresponding International Application No. PCT/EP2021/077490, filed Oct. 6, 2021,14 pages.

*Primary Examiner* — Amanda L Steinberg
*Assistant Examiner* — Philip C Edwards
(74) *Attorney, Agent, or Firm* — Christensen O'Connor Johnson Kindness PLLC

(57) ABSTRACT

An apparatus (100) for training and assisting gait of a person, comprises: a sensor (112; 140; 150) configured for being arranged in relation to a foot or leg of the person for sensing input related to movement of the foot; a foot sole stimulator (120) for providing a foot stimulation electrical signal to the foot sole for stimulating a nociceptive withdrawal reflex; a peroneal nerve stimulator (130) for providing a peroneal nerve stimulation electrical signal to the peroneal nerve for stimulating activation of foot dorsiflexor muscle; wherein at least the foot sole stimulator (120) is configured to provide the foot stimulation electrical signal in dependence of the input sensed by the sensor (112; 140; 150); and wherein the apparatus (100) is configured to be operated in at least two different modes for selectively activating at least one of the foot sole stimulator (120) or the peroneal nerve stimulator (130).

14 Claims, 2 Drawing Sheets

(52) U.S. Cl.
  CPC ..... *A61N 1/36031* (2017.08); *A61N 1/36034*
      (2017.08); *A61B 2562/0219* (2013.01)

(58) Field of Classification Search
  CPC .......... A61B 2562/0219; A61B 5/4052; A61B
      2505/09; A61B 2562/0247; A61B 5/4836
  See application file for complete search history.

(56) References Cited

U.S. PATENT DOCUMENTS

| | | |
|---|---|---|
| 2014/0094873 A1 | 4/2014 | Emborg et al. |
| 2014/0128939 A1 | 5/2014 | Embry et al. |
| 2020/0093400 A1* | 3/2020 | Hamner ............... A61N 1/0484 |

* cited by examiner

APPARATUS AND METHOD FOR TRAINING AND ASSISTING GAIT OF A PERSON

TECHNICAL FIELD

The present inventive concept relates to an apparatus and a method for training and assisting gait of a person.

BACKGROUND

A person suffering from deteriorated ability to walk is severely affected by such a condition. The ability to walk may for instance be caused by a disease or trauma to the central nervous system, such as stroke, spinal cord injury, and multiple sclerosis.

For such persons, gait rehabilitation is an important step to improve quality of life of the person. Gait rehabilitation may involve providing the person with an electrical stimulation, which may induce a nociceptive withdrawal reflex activating nerves of the person to cause a muscle contraction such that a foot is lifted. Electrical stimulation may thus be used in training for restoring ability of the person to send nerve signals for lifting the foot.

However, activation of nerves based on a nociceptive withdrawal reflex may be painful or at least uncomfortable to the person under gait rehabilitation. Therefore, it would be desired to provide gait rehabilitation that may avoid unnecessary discomfort to persons under gait rehabilitation.

SUMMARY

An objective of the present inventive concept is to provide an improved apparatus and method for gait rehabilitation and gait assistance. It is a particular objective of the present inventive concept to provide an apparatus and method for gait rehabilitation and gait assistance which may be used for augmenting training effect, enhancing assistive effect and avoiding discomfort to the person under gait rehabilitation.

These and other objectives of the present inventive concept are at least partly met by the invention as defined in the independent claims. Preferred embodiments are set out in the dependent claims.

According to a first aspect of the present inventive concept, there is provided an apparatus for training and assisting gait of a person, said apparatus comprising: a sensor configured for being arranged in relation to a foot or leg of the person for sensing input related to movement of the foot of the person; a foot sole stimulator for providing a foot stimulation electrical signal to the foot sole of the person for stimulating a nociceptive withdrawal reflex; a peroneal nerve stimulator for providing a peroneal nerve stimulation electrical signal to the peroneal nerve of the person for stimulating activation of foot dorsiflexor muscle; wherein at least the foot sole stimulator is configured to provide the foot stimulation electrical signal in dependence of the input sensed by the sensor; and wherein the apparatus is configured to be operated in at least two different modes for selectively activating at least one of the foot sole stimulator or the peroneal nerve stimulator.

Thanks to the apparatus according to the first aspect, different modes for training and assisting gait of a person may be provided by the same apparatus. Thus, the apparatus may be fit for being used continuously by a person by the apparatus being set to a suitable mode in dependence of current needs of the person. For instance, the user may not at all times need stimulation for activating a nociceptive withdrawal reflex. The nociceptive withdrawal reflex may help the person to properly lift the foot and also help cause knee and/or hip flexion. However, e.g. when walking around at home, the person may not need the help in knee and/or hip flexion and it may be sufficient to stimulate peroneal nerve for activating foot dorsiflexor muscles. Thus, the apparatus allows a versatile use such that the apparatus may be fitted to different needs during the day and may allow a person to only receive the amount of assistance that is needed while the person is using the same apparatus.

Many different scenarios could be conceived during which switching between different modes selectively activating at least one of the foot sole stimulator or the peroneal nerve stimulator would be beneficial. For instance, the foot sole stimulator could be activated when the person gets tired after having walked a lot during a day, or could be activated when conditions require more assistance, such as when the person is to climb stairs. Further, the apparatus is suitable for being used during a long period of time of gait rehabilitation and gait assistance, wherein for instance the foot sole stimulator may be activated during most of the time in a first period of gait rehabilitation but as the person's gait is improving the foot sole stimulator may be increasingly deactivated.

Since the apparatus supports gait assistance and training in many scenarios, the person may also be more likely to use the apparatus. This ensures that person's gait may improve faster and facilitates good rehabilitation and gait assistance.

In particular, the apparatus allows a foot sole stimulator to be deactivated, such that the potential discomfort of activating the nociceptive withdrawal reflex may be avoided, when not necessary. Still, thanks to the apparatus also including a peroneal nerve stimulator, gait training and assistance may be provided even if the foot sole stimulator is deactivated.

Thanks to the sensor, input related to movement of the foot of the person may be sensed. Such input may be provided in various ways but may provide an indication that a foot is about to be moved and/or that the person is trying/wants to move the foot such that a stimulation electrical signal may be triggered in dependence of the sensed input.

According to an embodiment, the apparatus is configured to be operated in a mode wherein the apparatus is used in combination with a robot rehabilitation device.

A robot rehabilitation device is an external device that can be attached to the person. The robot rehabilitation device may provide an external structural mechanism to the person, wherein the mechanism is provided with joints and links so as to enable movement corresponding to human gait. The robot rehabilitation device may perform repetitive gait movement when attached to the person so as to bring the person's legs to move correspondingly and hence aid in gait rehabilitation. The robot rehabilitation device may thus have a control system for controlling movement of the external structural mechanism.

The apparatus may be configured to allow the foot sole stimulator and/or peroneal nerve stimulator to provide a respective stimulation electrical signal synchronously with movement by the external structural mechanism of the robot rehabilitation device. Thus, a control signal for triggering a stimulation electrical signal by the foot sole stimulator and/or the peroneal nerve stimulator may be provided by the control system of the robot rehabilitation device. In this context, any control of the stimulation electrical signal of the foot sole stimulator and/or peroneal nerve stimulator by the sensor may be deactivated during use of the apparatus in combination with the robot rehabilitation device.

As mentioned, the apparatus allows a versatile use and the apparatus being further able to be used in combination with a robot rehabilitation device further increases versatility of the apparatus.

According to an embodiment, the sensor for sensing input related to movement of the foot of the person may be a foot pressure sensor, which is configured to sense a pressure asserted by the foot of the person against ground as an indication that the foot is being moved or is about to be moved. The apparatus may comprise more than one foot pressure sensor, which may be configured to be arranged at different positions beneath the foot of the person. Thus, using more than one foot pressure sensor it may be possible to sense what part of a foot is lifted or pressed against ground, e.g. using a sensor arranged at a heel and a sensor arranged at a forefoot.

The pressure asserted against ground may indicate when gait assistance is needed and may allow determining a gait phase. For instance, when a pressure decreases, it may be an indication that the person needs help in lifting the foot during a swing phase, such that a detection of decreased pressure by the pressure sensor may be used for activating a stimulation to aid gait of the person. However, it should also be realized that a person suffering from impaired gait may not be able to assert a large pressure at any time, e.g. a person suffering from foot drop. Hence, it is not necessarily a decrease in pressure sensed by the foot sensor that provides an indication that stimulation is to be activated. Thus, a signal from a foot pressure sensor may be used in different ways for providing input in activating a foot sole stimulator and/or a peroneal nerve stimulator. The manner of using the signal from the foot pressure sensor may be set individually for the person.

According to another embodiment, the sensor for sensing input related to movement of the foot of the person may be an inertial sensor configured for being arranged on or beneath the foot of the person or on a leg of the person. The inertial sensor may be configured for sensing a movement of the foot and/or leg of the person as an indication that the foot is being moved or is about to be moved.

According to another embodiment, the sensor for sensing input related to movement of the foot of the person may be a muscle activity sensor for sensing muscle activity in the leg of the person. The muscle activity sensor may thus be configured to sense activity in a muscle for moving the foot of the person as an indication that the foot is being moved or is about to be moved.

It should be realized that the apparatus may comprise all of the at least one foot pressure sensor, the inertial sensor and the muscle activity sensor. Input sensed by any of these sensors or any combination of input sensed by these sensors may be used for controlling the foot stimulation electrical signal and the peroneal nerve stimulation electrical signal, respectively. The foot stimulation electrical signal and the peroneal nerve stimulation electrical signal may each be controlled by using input from the same sensors or by using input from different sensors.

As used herein, the phrase "at least the foot sole stimulator is configured to provide the foot stimulation electrical signal in dependence of the input sensed by the sensor" should be construed such that the foot sole stimulator is controlled to provide the foot stimulation electrical signal in dependence of the sensed input and the peroneal nerve stimulator may or may not be controlled to provide the peroneal nerve stimulation electrical signal in dependence of the sensed input.

It should be realized that the apparatus may be configured to be operated in more than two different modes. In each of the modes, at least one of the foot sole stimulator or the peroneal nerve stimulator is active. It should be realized that both the foot sole stimulator and the peroneal nerve stimulator may be active in one mode. As used herein, a mode of operation defines which of the foot sole stimulator and/or the peroneal nerve stimulator are active. The mode of operation may also define a sensor signal, which is used for controlling activation of the foot sole stimulator and/or the peroneal nerve stimulator, such that two different modes may differ only in which sensor signal is used for controlling activation. However, solely a change in intensity of the foot stimulation electrical signal or the peroneal nerve stimulation electrical signal does not imply that a mode of operation of the apparatus is changed. Thus, within a mode of operation, intensity of the foot stimulation electrical signal and/or the peroneal nerve stimulation electrical signal may be varied.

According to an embodiment, the sensor comprises a foot pressure sensor configured for being arranged beneath a foot of the person for sensing a pressure asserted by the foot of the person, wherein the foot sole stimulator and/or the peroneal nerve stimulator are configured to provide the foot stimulation electrical signal and the peroneal nerve stimulation electrical signal, respectively, in dependence of the sensed pressure by the foot pressure sensor.

Hence, according to an embodiment, both the peroneal nerve stimulator and the foot sole stimulator may be controlled in dependence of the at least one foot pressure sensor. This implies that the foot pressure sensor may be re-used both for controlling the peroneal nerve stimulator and the foot sole stimulator.

According to an embodiment, the apparatus further comprises an inertial sensor configured for being arranged on or beneath the foot of the person or on a leg of the person for sensing a movement of the foot and/or leg of the person, wherein the foot sole stimulator and/or the peroneal nerve stimulator are configured to provide the foot stimulation electrical signal and the peroneal nerve stimulation signal, respectively, in dependence of a sensed movement by the inertial sensor.

The peroneal nerve stimulator may be suitable for use in assisting gait, e.g. when the person needs aid to dorsiflex the foot but may not need full help for lifting the foot. Thus, the gait may not be very severely impaired, and it may therefore be possible to sense a movement based on an inertial sensor, as the person may start moving the foot and/or leg without help from the apparatus. Therefore, it may be possible to use the inertial sensor as input such that the peroneal nerve stimulation electrical signal may be provided in dependence of a sensed movement by the inertial sensor.

It should be realized that also the foot sole stimulator may use input from the inertial sensor such that the foot stimulation electrical signal may be provided in dependence of a sensed movement by the inertial sensor.

It should be realized that the apparatus may comprise both at least one foot sensor and the inertial sensor. Both the at least one foot sensor and the inertial sensor may be used for controlling the peroneal nerve stimulation electrical signal and/or the foot stimulation electrical signal. The peroneal nerve stimulation electrical signal and/or the foot stimulation electrical signal may thus be provided in dependence of a sensed movement by the inertial sensor and a sensed pressure by the foot pressure sensor. Alternatively, control of the peroneal nerve stimulator and/or the foot stimulation electrical signal may be switched, e.g. in different modes of the apparatus, such that the at least one foot pressure sensor and the inertial sensor are selectively activated to be used for controlling the peroneal nerve stimulator and/or the foot stimulation electrical signal in different modes of the apparatus.

According to an embodiment, the apparatus is configured to be operated in a reflex mode, wherein the foot sole stimulator is active while the peroneal nerve stimulator is inactive, in a dorsiflexor mode, wherein the peroneal nerve stimulator is active while the foot sole stimulator is inactive and in a combined mode, wherein both the peroneal nerve stimulator and the foot sole stimulator are active.

Thus, the apparatus may be set to at least three different modes, which may be useful in different situations.

The reflex mode may be beneficially used in beginning of gait rehabilitation after e.g. a stroke. The reflex mode may thus be used for retraining the person when gait is severely impaired, and the person may not be able to move the leg and/or foot much without nociceptive reflex activation. However, the reflex mode may also be beneficially used in certain situations when the person has regained gait ability, but gait may still be impaired. For instance, during training sessions for improving the gait, the reflex mode may be useful.

The dorsiflexor mode may be useful when the needs aid to dorsiflex the foot, but the person has ability to lift the foot and may be capable of some hip flexion and/or knee flexion during gait. Thus, the dorsiflexor mode may be used when the gait is impaired to improve dorsiflexing of the foot. While the reflex mode may be painful or provide discomfort to the person, the dorsiflexor mode does not necessarily cause any discomfort to the person. Therefore, the dorsiflexor mode may be beneficially used, when the reflex mode is not needed, in order to aid gait of the person.

The combined mode may be useful for selective activation by a person that is mainly using the dorsiflexor mode. Thus, the combined mode may be used when the person gets fatigued or in a challenging situation, such as when the person needs better ground clearance of the foot to e.g. pass a doorstep, walk uphill or climb stairs.

According to an embodiment, the foot sole stimulator is configured to be controlled to provide a first magnitude of the foot stimulation electrical signal in the combined mode and a second magnitude of the foot stimulation electrical signal in the reflex mode, wherein the first magnitude is lower than the second magnitude.

It may be conceivable that the magnitude of the foot stimulation electrical signal need not be as high in the combined mode as in the reflex mode. Thus, if it would be sufficient to use a lower magnitude in the combined mode in order to achieve a desired response to aid the gait of the person, such lower magnitude of the foot stimulation electrical signal may be beneficially used to reduce discomfort of the person. It should also be realized that the magnitude of the foot stimulation electrical signal may be controlled within a mode of operation, such that the person using the apparatus may set the magnitude to be used in order for the aid provided by the apparatus to be sufficient. However, in other embodiments, the magnitude of the foot stimulation electrical signal may be equal in the combined mode and in the reflex mode.

According to an embodiment, the apparatus further comprises a muscle activity sensor configured for being arranged on a leg of the person for sensing muscle activity in the leg of the person, wherein the apparatus is further configured to be operated in a direct mode, wherein the peroneal nerve stimulator is configured to provide the peroneal nerve stimulation electrical signal in dependence of the sensed muscle activity by the muscle activity sensor.

The direct mode may be useful when the person has voluntary muscle activity for activating foot dorsiflexor muscles, but there is still a need for aid by the apparatus. Hence, the muscle activity for dorsiflexing the foot may be sensed and may be directly used for also controlling the aid to be provided by the peroneal nerve stimulator in assisting the gait of the person. Thus, an effect of the person's own ability to activate dorsiflexor muscles may be amplified by the peroneal nerve stimulator providing stimulation based on the voluntary muscle activity of the person. The direct mode may thus provide a more natural way of performing gait and may possibly improve awareness and ability of the person to activate the dorsiflexor muscles naturally.

As described above, the muscle activity sensor may be used for providing input related to movement of the foot of the person. This input may be used by itself or in combination with input from other sensors for controlling any of the foot stimulation electrical signal and the peroneal nerve stimulation electrical signal. In particular, the peroneal nerve stimulation signal may in embodiments, or in modes of operation of the apparatus, be provided in dependence of a sensed muscle activity by the muscle activity sensor, a sensed movement by the inertial sensor and a sensed pressure by the foot pressure sensor. However, other combinations of use of the input from the sensors may also be conceivable, such as the sensors being separately used in different modes of operation of the apparatus.

According to an embodiment, the apparatus further comprises a control unit for controlling the apparatus to be operated in a selected mode.

Thus, the control unit may select the mode of operation of the apparatus. The control unit may receive input for selecting the mode of operation.

The control unit may also be configured to control operation of the apparatus, when a mode of operation has been selected. In this respect, the control unit may be configured to receive input from sensors, such as the at least one foot pressure sensor, the inertial sensor and/or the muscle activity sensor. The control unit may further be configured to transmit control signals for controlling stimulation by the foot sole stimulator and/or the peroneal nerve stimulator. The control unit may thus control timing and/or magnitude of the stimulation electrical signal provided by the foot sole stimulator and/or the peroneal nerve stimulator.

According to an embodiment, the control unit is configured to receive manual input for selecting a current mode of the apparatus.

Thus, the person wearing the apparatus may select the mode of operation of the apparatus by providing input to the control unit. The manual input may be provided through a user interface on the apparatus. However, according to an alternative, the manual input may be provided on a remote unit, which may communicate the manual input to the control unit, e.g. through wireless communication.

The person may use the possibility to manually select the mode of operation in order to adapt the mode of operation of the apparatus to the person's desire and needs. For instance, when becoming fatigued or when facing a challenging environment, the person may manually switch the operation from the dorsiflexor mode to the reflex mode or the combined mode.

According to an embodiment, the control unit further comprises a mode detection unit, which is configured to use input from the sensor for sensing input related to movement of the foot of the person to automatically detect a suitable mode of operation of the apparatus for selecting a current mode of the apparatus.

Thus, the control unit may itself determine which mode of operation of the apparatus may be suitable based on sensor input. Thus, selection of the current mode of the apparatus may be based on the suitable mode automatically detected by the control unit.

This implies that the person need not even give manual input for selecting the mode of operation, but the apparatus may instead itself set the proper mode of operation based on input relating to the gait of the person. This would facilitate usability of the apparatus, as the person need not give manual input for selecting mode of operation. In particular, it would be beneficial when the person is walking through a shifting environment and switching of mode of operation of the apparatus is to be performed relatively frequently.

According to an embodiment, the control unit is configured to receive input from additional sensors, such as a manual switch to be operated by the user or caretaker, for controlling the apparatus when the user is not walking, e.g. for training purposes, or as a manual control option in cases where a foot pressure sensor, inertial sensor or a muscle activity sensor is inadequate.

Thus, when desired, manual input may be provided to the control unit for controlling operation of the apparatus manually in particular situations.

According to an embodiment, the control unit is configured to receive input from additional sensors, such as an additional inertial sensor configured to be arranged on a healthy leg of the person, for controlling operation of the apparatus and/or providing feedback of gait of the person.

Thanks to receiving input from additional sensors, the control unit may have more information on which to base detection of a suitable mode of operation and/or for controlling stimulation by the foot sole stimulator and/or the peroneal nerve stimulator. The additional sensors may thus help the control unit to improve proper detection of the suitable mode of operation and to improve control of stimulation.

According to an embodiment, the control unit further comprises a gait quality detection module for analyzing gait quality based on sensor input.

The gait quality detection module may use input from sensors of the apparatus and also from additional sensors, in order to determine a gait quality of the person. Thanks to detection of gait quality, a functionality of the apparatus may be assessed, such that settings of the apparatus may be changed if the gait quality is insufficient or not improving sufficiently during gait rehabilitation and gait assistance.

Further, the detection of gait quality may also or alternatively be used as input for detecting a suitable mode of operation. Thus, if the gait quality detection module detects that gait quality is increasing or decreasing, the control unit may use such detection for automatically detecting a suitable mode of operation. It should however be realized that the control unit may be configured to automatically detect a suitable mode of operation without necessarily a gait quality being assessed.

According to an embodiment, the apparatus further comprises a communication unit for wireless communication with a remote unit.

The apparatus being configured to communicate with a remote unit may facilitate interaction of a user with the apparatus. While the apparatus may be arranged beneath a foot and along a leg of a person, the communication with a remote unit allows the person to interact with the apparatus without bending to physically touch the apparatus arranged on the leg.

The remote unit may for instance be any portable device which the person may carry. For instance, the remote unit may be a smartphone or other wearable device with which user interaction is facilitated. The person wearing the apparatus may thus control the apparatus through a user interface in the remote unit, such as through a dedicated software being executed on the remote unit. Also, the person wearing the apparatus may receive input from the apparatus to the remote unit, e.g. for displaying information, such as a status of the apparatus and/or detected gait quality. The remote unit may not necessarily be a unit that is carried by the person wearing the apparatus. Alternatively, the apparatus may communicate with the remote unit via a computer and/or telecommunication network, such that the remote unit may be placed anywhere. For instance, the apparatus may be configured to communicate information of status and/or gait quality to a remote user, such as a caregiver, allowing the caregiver to give advice to the person wearing the apparatus on use of the apparatus.

According to an embodiment, the apparatus further comprises a carrier being configured to be arranged beneath the foot of the person and along at least a lower leg of the person, wherein the sensor for sensing input related to movement of the foot of the person, the foot sole stimulator, the peroneal nerve stimulator and the control unit are mounted in or on the carrier.

Thus, the carrier may be configured to be arranged on the person wearing the apparatus and components of the apparatus may be mounted in or on the carrier for arranging the components in desired relation to the person when the carrier is arranged on the person. In particular, the sensor, the foot sole stimulator and the peroneal nerve stimulator may be properly arranged in relation to the person when the apparatus is worn, but it should be realized that other sensors and other components interacting with the person may also be properly arranged by the carrier when the apparatus is worn.

The carrier may have a shape and size to facilitate attachment of the carrier beneath the foot and along at least the lower leg of the person. Thus, the carrier may be shaped so as to control the relation to foot and leg of the person so as to facilitate that the apparatus will be properly arranged by the person when the person arranges the carrier onto the leg and beneath the foot.

According to an embodiment, the carrier comprises a spring-loaded brace configured to be arranged beneath the foot of the person to reduce foot drop.

Thus, the carrier may also aid gait of the person using the spring-loaded brace to reduce effect of foot drop of the person during gait. The spring-loaded brace may thus act in concert with the stimulation by the foot sole stimulator and/or the peroneal nerve stimulator in aiding gait of the person.

According to an embodiment, the foot sole stimulator comprises at least one foot electrode configured to be arranged in contact with a foot sole of the person and a pulse generator for generating the foot stimulation electrical signal, and wherein the peroneal nerve stimulator comprises at least one leg electrode configured to be arranged in contact with a leg of the person for providing the peroneal nerve stimulation electrical signal to the peroneal nerve and a pulse generator for generating the peroneal nerve stimulation electrical signal, wherein the pulse generator of the foot sole stimulator and the pulse generator of the peroneal nerve stimulator may optionally be shared.

The stimulation electrical signals may be provided between pairs of electrodes. The two electrodes used in providing a stimulation signal to the person may be arranged relatively close to each other such that a stimulus site is local, which may be beneficial. The apparatus may comprise a plurality of electrodes such that the pair of electrodes to be used in providing a particular stimulation may be selected among the plurality of electrodes. The apparatus may also comprise a set of electrodes, at least two, dedicated for the foot sole stimulator for providing the foot stimulation electrical signal and a set of electrodes, at least two, dedicated for the peroneal nerve stimulator for providing the peroneal nerve stimulation electrical signal.

One of the electrodes in a pair of electrodes used for providing the stimulation electrical signal may be a ground electrode. In an embodiment, the apparatus may comprise a ground electrode which is shared by the foot sole stimulator and the peroneal nerve stimulator.

The peroneal nerve stimulator and the foot sole stimulator need not necessarily simultaneously provide the foot stimulation electrical signal and the peroneal nerve stimulation electrical signal. This implies that pulse generator may be shared in order to reduce a number of components in the apparatus. Even in the combined mode, when a stimulation electrical signal is to be provided both to the foot sole and the peroneal nerve, a single pulse generator may provide the stimulation electrical signals in such a fast sequence (very short time interval between the signals) that a simultaneous effect to the person may be provided to allow the peroneal nerve stimulation and the foot stimulation to act in concert for aiding the gait of the person.

According to a second aspect of the present inventive concept, there is provided a method for training and assisting gait of a person, said method comprising: detecting input to select a mode of operation of an apparatus for training and assisting gait of a person between at least a reflex mode and a dorsiflexor mode, wherein a foot sole stimulator and a peroneal nerve stimulator of the apparatus are selectively activated in dependence of a selected mode of operation; in case the apparatus is selected to be operated in the reflex mode: setting the foot sole stimulator to be active and the peroneal nerve stimulator to be inactive; and based on input from a sensor sensing input related to movement of the foot of the person, controlling stimulation by foot sole stimulation electrical signals from the foot sole stimulator to the foot sole of the person for stimulating a nociceptive withdrawal reflex during gait of the person; in case the apparatus is selected to be operated in the dorsiflexor mode: setting the foot sole stimulator to be inactive and the peroneal nerve stimulator to be active; and based on input from a sensor sensing input related to movement of the foot of the person, controlling stimulation by peroneal nerve stimulation electrical signals from the peroneal nerve stimulator to the peroneal nerve of the person for stimulating activation of foot dorsiflexor muscle.

Effects and features of this second aspect are largely analogous to those described above in connection with the first aspect. Embodiments mentioned in relation to the first aspect are largely compatible with the second aspect.

Thanks to the method according to the second aspect, different modes for training and assisting gait of a person may be provided by the same apparatus. Thus, the apparatus may be fit for being used continuously by a person by the apparatus being set to a suitable mode in dependence of current needs of the person. This facilitates providing an efficient training and assistance of gait of a person.

According to an embodiment, the method further comprises receiving sensor input relating to gait quality and analyzing gait quality based on the sensor input, wherein the gait quality may be used as input to select a mode of operation of the apparatus.

The analysis of gait quality may use input from sensors of the apparatus and also from additional sensors, in order to determine a gait quality of the person. Thanks to analysis of gait quality, a functionality of the apparatus may be assessed, such that settings of the apparatus may be changed if the gait quality is insufficient or not improving sufficiently during gait rehabilitation and gait assistance.

Further, the analysis of gait quality may be used for selecting mode of operation of the apparatus. Thus, if it is detected that gait quality is increasing or decreasing, such detection may be used for automatically detecting a suitable mode of operation.

According to a third aspect of the present inventive concept, there is provided a computer program product comprising computer-readable instructions such that when executed on a processing unit the computer-readable instructions will cause the processing unit to perform the method according to the second aspect.

Effects and features of this third aspect are largely analogous to those described above in connection with the first and second aspects. Embodiments mentioned in relation to the first and second aspects are largely compatible with the third aspect.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
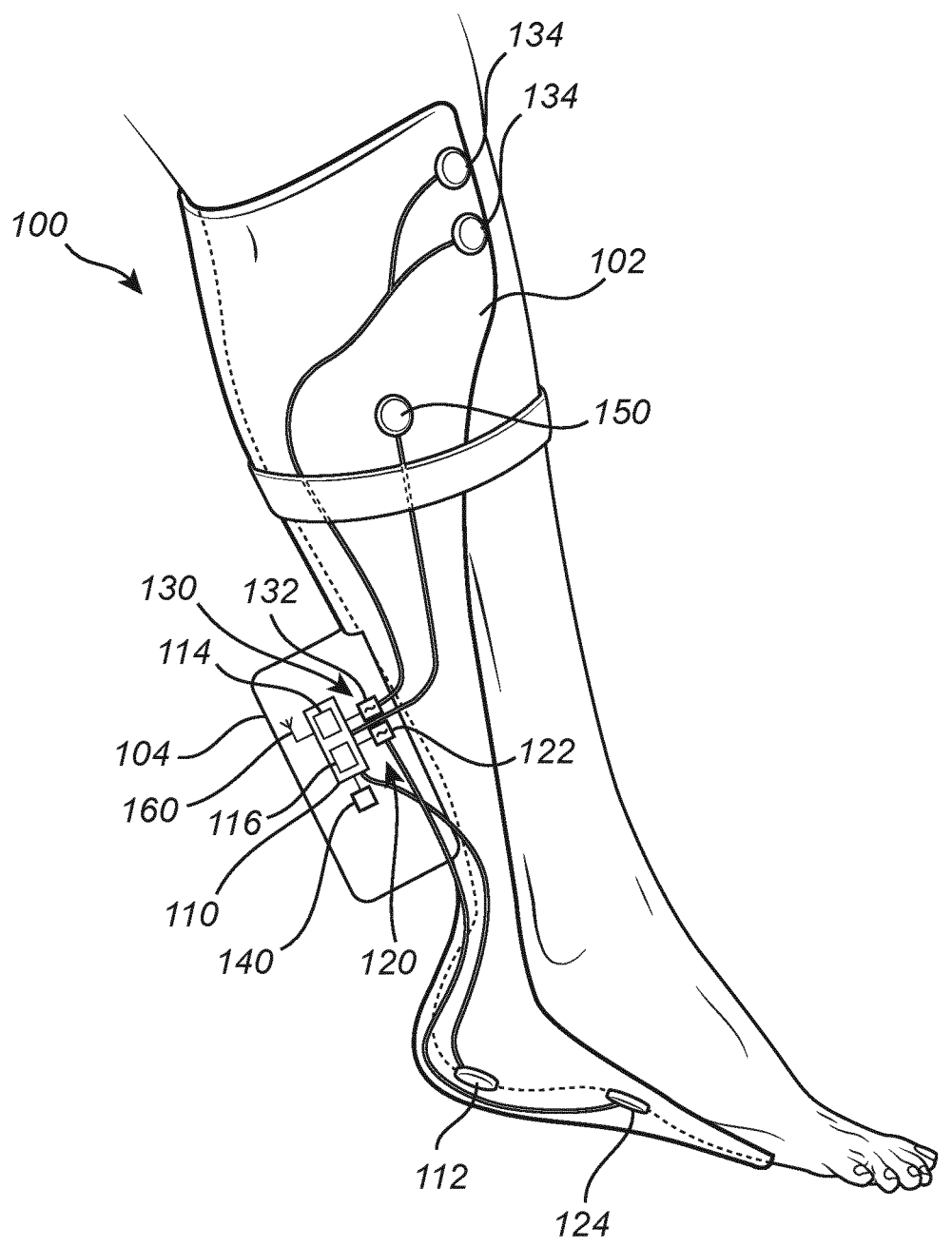
FIG. 1 is a schematic view of an apparatus according to an embodiment.

FIG. 1 illustrates an apparatus 100 for training and assisting gait of a person. The apparatus 100 may comprise a carrier 102, which has a size and shape to be fit to be arranged beneath a foot of a person and along at least a part of a lower leg of the person. Attachment of the carrier 102 on a person may be guided by the shape of the carrier 102 so as to aid the person in properly and quickly arranging the carrier 102 beneath the foot and along the leg. Further, the carrier 102 may comprise one or more attachment elements, such as one or more straps which may be configured to be arranged around the leg and/or ankle and/or foot. The straps may have mating connections, such as hook and loop fasteners, for attaching the straps around the leg and/or ankle and/or foot.

The carrier 102 may define positions of components of the apparatus 100 in relation to the person. Thus, components of the apparatus 100 may be mounted in fixed positions on the carrier 102 such that the arrangement of the carrier 102 on the person will also arrange the components in a desired relation to the person.

The apparatus 100 may comprise a control unit 110, which may be configured to control functionality of components of the apparatus 100 and which may communicate with the components for receiving input and/or controlling functions of components based on received input. However, it should be realized that components of the apparatus 100 may communicate directly with each other in addition to or instead of communication via the control unit 110. In this regard, the control unit 110 may not strictly be necessarily included in the apparatus 100.

The control unit 110 may be implemented as a general-purpose processing unit, such as a central processing unit (CPU), which may execute the instructions of one or more computer programs in order to implement the functionality of the control unit 110. The control unit 110 may alternatively be implemented as firmware arranged e.g. in an embedded system, or as a special-purpose circuitry for providing only specific logical operations. Thus, the control unit 110 may be provided in the form of an ASIC or FPGA.

The control unit 110 may further comprise a non-volatile memory. The memory may store application(s), which may be loaded into a working memory of the control unit 110 for controlling the processing performed by the control unit 110.

It should also be realized that the control unit 110 may be implemented as one or more modules. When including several modules, the modules may be dedicated for different parts of the functionality of the control unit 110.

The apparatus 100 may further comprise at least one foot pressure sensor 112. The at least one foot pressure sensor 112 may be configured for being arranged beneath a foot of the person. For instance, the at least one foot pressure sensor 112 may be mounted on a surface of the carrier 102 in a portion of the carrier 102 dedicated to being arranged beneath the foot of the person. The at least one foot pressure sensor 112 may be mounted on the carrier 102 so as to face the foot sole of the person when the carrier 102 is arranged on the person.

The at least one foot pressure sensor 112 may thus be configured to receive an asserted pressure by the person and may be configured to transform the asserted pressure to an electrical signal proportional to the amount of asserted pressure.

The at least one foot pressure sensor 112 may be connected to the control unit 110 for transmitting measured pressure signals to the control unit 110.

The apparatus 100 may comprise a foot pressure sensor 112 arranged at a heel for sensing a pressure asserted by the heel of the person against ground. As the heel is normally lifted first during a swing phase of gait of a person, a heel sensor may be appropriately used for determining a phase of gait of the person, such as determining when a foot is lifted or is desired to be lifted from ground. However, it should be realized that the foot pressure sensor 112 may be arranged in a different relation to the foot sole of the person. Further, the apparatus 100 may comprise a plurality of foot pressure sensors 112 and the control unit 110 may use input from the plurality of foot pressure sensors 112 in order to determine a phase of gait of the person. The control unit 110 may use a dedicated algorithm for comparing pressures from a plurality of foot pressure sensors 112 in order to determine a phase of gait of the person or at least to determine when stimulation for aiding gait is to be provided.

The apparatus 100 may further comprise a foot sole stimulator 120 and a peroneal nerve stimulator 130.

The foot sole stimulator 120 may be configured to provide a foot stimulation electrical signal to the foot sole of the person. The foot stimulation electrical signal may have a sufficient magnitude to stimulate a nociceptive withdrawal reflex causing the foot to be lifted by hip flexion and/or knee flexion and thus providing training and/or assistance of gait of the person.

The peroneal nerve stimulator 130 may be configured to provide a peroneal nerve stimulation electrical signal to the peroneal nerve of the person. The peroneal nerve stimulation electrical signal may have a sufficient magnitude to stimulate the peroneal nerve to activate the foot dorsiflexor muscles such that the foot is lifted by ankle dorsiflexion and thus providing training and/or assistance of gait of the person.

Each of the foot sole stimulator 120 and the peroneal nerve stimulator 130 may comprise a pulse generator 122, 132 for generating an electrical signal. The pulse generator 122, 132 may generate an electrical signal in the form of a pulse with an amplitude, wave form and duration sufficient to generate a desired response of the person. The amplitude, wave form and/or duration of the electrical signal generated by the pulse generator 122, 132 may be adjusted based e.g. on a control signal from the control unit 110.

The foot sole stimulator 120 and the peroneal nerve stimulator 130 may share the same pulse generator such that the foot stimulation electrical signal and the peroneal nerve stimulation electrical signal are generated by the same pulse generator. However, alternatively, each of the foot sole stimulator 120 and the peroneal nerve stimulator 130 may comprise a separate pulse generator 122, 132.

The pulse generator 122 of the foot sole stimulator 120 may be connected by wires to electrodes 124 for transferring the generated foot stimulation electrical signal to the electrodes 124. The foot sole stimulator 120 may comprise a plurality of electrodes 124 and the foot sole stimulator 120 may be configured to select two electrodes among the plurality of electrodes 124 that are to be used for providing the foot stimulation electrical signal to the foot of the person. The foot sole stimulator 120 may thus at least comprise two electrodes 124.

The pulse generator 132 of the peroneal nerve stimulator 130 may be connected by wires to electrodes 134 for transferring the generated peroneal nerve stimulation electrical signal to the electrodes 134. The peroneal nerve stimulator 130 may comprise a plurality of electrodes 134 and the peroneal nerve stimulator 130 may be configured to select two electrodes among the plurality of electrodes 134 that are to be used for providing the peroneal nerve stimulation electrical signal to the peroneal nerve of the person. The peroneal nerve stimulator 130 may thus at least comprise two electrodes 134.

One of the electrodes 124, 134 for each of the foot sole stimulator 120 and the peroneal nerve stimulator 130 may be a ground electrode, whereas the other electrode 124, 134 is arranged to receive the signal from the pulse generator 122, 132. However, in one embodiment, a ground electrode may be shared by the foot sole stimulator 120 and the peroneal nerve stimulator 130 such that the foot sole stimulator 120 and the peroneal nerve stimulator 130 may only need to comprise one additional electrode 124, 134 each.

The electrodes 124, 134 may be mounted on the carrier 102 for defining a position of the electrodes 124, 134 in relation to the foot sole of the person and the peroneal nerve of the person, respectively. The electrodes 124, 134 may comprise a metal or conducting surface facing skin of the person and may possibly be provided with a gel for improving electrical connection to the skin. A potential difference between two electrodes 124, 134 will cause a current to pass through tissue between the electrodes 124, 134. The foot sole stimulator 120 may thus pass the foot stimulation electrical signal through tissue and stimulate a response in the form of a nociceptive withdrawal reflex. The peroneal nerve stimulator 130 may pass the peroneal nerve stimulation electrical signal through tissue to the peroneal nerve and stimulate activation of foot dorsiflexor muscles.

The electrodes 124, 134 may be configured to be re-used, but regardless whether electrodes 124, 134 are intended for one-time use or intended to be re-used, the electrodes 124, 134 may be mounted in the carrier 102 to allow simple replacement of electrodes 124, 134 to improve lifetime of the carrier 102.

Each of the foot sole stimulator 120 and the peroneal nerve stimulator 130 may be triggered to generate the foot stimulation electrical signal and the peroneal nerve electrical signal, respectively, based on input from one or more sensors providing indications of a proper timing of the stimulation electrical signal.

The foot sole stimulator 120 may be configured to provide the foot stimulation electrical signal in dependence of a sensed pressure by the at least one foot pressure sensor 112. For instance, a sensed pressure decreasing below a threshold value may be an indication that the foot is about to be lifted or that the person desires to lift the foot and such decrease of the sensed pressure by the at least one foot pressure sensor 112 may be used for triggering generation of the foot stimulation electrical signal. However, it should be realized that a more advanced algorithm analyzing the sensed pressure from one or more foot pressure sensors 112 may be used for accurately determining when the foot stimulation electrical signal is to be provided for person's with different levels of gait impairment. The control unit 110 may be configured to determine that the foot stimulation electrical signal is to be generated and send a control signal to the foot sole stimulator 120 triggering generation of the foot stimulation electrical signal. However, the foot sole stimulator 120 may alternatively receive measurements from the at least one foot pressure sensor 112 and may be configured to determine that the foot stimulation electrical signal is to be generated.

The peroneal nerve stimulator 130 may also be configured to provide the peroneal nerve stimulation electrical signal in dependence of a sensed pressure by the at least one foot pressure sensor 112. In this regard, the sensed pressure by the at least one foot pressure sensor 112 may be processed in the same manner for triggering generation of the peroneal nerve stimulation electrical signal and the foot stimulation electrical signal. The peroneal nerve stimulator 130 may receive a control signal to trigger generation of the peroneal nerve stimulation electrical signal from the control unit 110. Alternatively, the peroneal nerve stimulator 130 may receive measurements from the at least one foot pressure sensor 112 and may be configured to determine that the peroneal nerve stimulation electrical signal is to be generated.

The foot sole stimulator 120 and/or the peroneal nerve stimulator 130 may be configured to provide the foot stimulation electrical signal and the peroneal nerve stimulation electrical signal, respectively, in dependence of input from other sensors than the at least one foot pressure sensor 112. Thus, the foot sole stimulator 120 and the peroneal nerve stimulator 130, respectively, need not necessarily use input from the at least one foot pressure sensor 112 to trigger generation of the foot stimulation electrical signal and the peroneal nerve stimulation electrical signal, respectively.

The foot sole stimulator 120 may be configured to provide the foot stimulation electrical signal in dependence of additional input from other sensors than the at least one foot pressure sensor 112. However, since the foot stimulation electrical signal is intended to cause a nociceptive withdrawal reflex, which may be needed when gait is severely impaired, input from the foot pressure sensor 112 may be beneficially used to trigger generation of the foot stimulation electrical signal. For severely impaired gait, there may not be sufficient movement of the leg and/or foot in order to allow other sensors to properly detect that a foot should be lifted and hence, in some embodiments, the at least one foot pressure sensor 112 may be needed in order to allow the foot stimulation electrical signal to be appropriately generated for a person suffering from severely impaired gait.

The apparatus 100 may further comprise an inertial sensor 140, which may be mounted on the carrier 102 in order to be arranged on or beneath the foot of the person or on a leg of the person.

The carrier 102 may comprise a housing 104, which is arranged on the carrier 102 such that the housing 104 is placed at the ankle of the person when the carrier 102 is worn. The housing 104 may form a small protrusion from the carrier 102 and for comfort this may beneficially be placed at the ankle of the person. Also, arrangement of the inertial sensor 140 at the ankle may be a suitable position for sensing a movement of the foot and/or leg of the person.

The housing 104 may be configured to enclose the inertial sensor 140 and also the control unit 110, the pulse generators 122, 132 of the foot sole stimulator 120 and the peroneal nerve stimulator 130. Further, the housing 104 may be configured to enclose a battery for providing power to the apparatus 100 and a communication unit 160 for communicating with a remote unit.

The inertial sensor 140 may be configured to sense a movement of the foot and/or leg of the person. For instance, the inertial sensor 140 may include a gyroscope and/or an accelerometer for sensing movements.

The inertial sensor 140 may thus be configured to detect when a foot is lifted in order to determine an instant in time when the person may need assistance from the apparatus 100 to properly lift the foot and/or to activate dorsiflexor muscles.

Input from the inertial sensor 140 may be used in addition to input from the at least one foot pressure sensor 112 for determining that the foot stimulation electrical signal is to be generated.

Input from the inertial sensor 140 may be used in addition to input from the at least one foot pressure sensor 112 for determining that the peroneal nerve stimulation electrical signal is to be generated.

Alternatively, input from the inertial sensor 140 may be used without input from the at least one foot pressure sensor 112 for determining that the foot stimulation electrical signal or the peroneal nerve stimulation electrical signal is to be generated. The input from the inertial sensor 140 may thus be used solely for determining that the foot stimulation electrical signal or the peroneal nerve stimulation electrical signal is to be generated or may alternatively be used together with input from other sensors for determining that the foot stimulation electrical signal or the peroneal nerve stimulation electrical signal is to be generated.

The apparatus 100 may further comprise a muscle activity sensor 150, which may be mounted on the carrier 102 in order to be arranged on a leg of the person for sensing muscle activity in the leg of the person.

The muscle activity sensor 150 may be configured to sense a muscle activity in the leg of the person related to voluntary muscle activity for activating dorsiflexor muscles. For instance, the muscle activity sensor 150 may comprise an electromyography sensor for measuring muscle activity. The muscle activity sensor 150 may comprise electrode(s), which may be mounted on the carrier 102 for defining a position of the electrode(s) in relation to muscles in the leg for detecting muscle activity for activating dorsiflexor muscles. The electrode(s) may be arranged on the Tibial Anterior muscle for detecting muscle activity for activating dorsiflexor muscles. The electrode(s) may detect an electrical signal in the muscle and may transfer the electrical signal to a signal processor for identifying muscle activity.

The electrode(s) for sensing muscle activity may be shared with the electrodes 134 of the peroneal nerve stimulator 130. Thus, the electrodes may be arranged such that both muscle activity for activating dorsiflexor muscles may be detected and the peroneal nerve may be stimulated by the peroneal nerve stimulation signal. However, the muscle activity sensor 150 and the peroneal nerve stimulator 130 may preferably comprise different electrodes such that the electrodes may be properly arranged for the respective purposes.

The muscle activity sensor 150 may thus be configured to detect when a voluntary muscle signal for activating dorsiflexor muscles is generated in order to determine an instant in time when the person may need assistance from the apparatus 100 to properly lift the foot and/or to improve activation of dorsiflexor muscles.

Input from the muscle activity sensor 150 may be used in addition to input from the at least one foot pressure sensor 112 and/or input from the inertial sensor 140 for determining that the foot stimulation electrical signal is to be generated.

Input from the muscle activity sensor 150 may be used in addition to input from the at least one foot pressure sensor 112 and/or input from the inertial sensor 140 for determining that the peroneal nerve stimulation electrical signal is to be generated.

Alternatively, the input from the muscle activity sensor 150 may be used solely for determining that the foot stimulation electrical signal or the peroneal nerve stimulation electrical signal is to be generated or may alternatively be used together with input from yet other sensors for determining that the foot stimulation electrical signal or the peroneal nerve stimulation electrical signal is to be generated.

The apparatus 100 is configured to be operated in different modes for adapting stimulation to needs of the person. Thus, the apparatus 100 is versatile and fits providing gait training and/or assistance in different stages of gait rehabilitation and gait assistance. Also, the apparatus 100 may be dynamically adapted to provide gait training and/or assistance in different environments posing different challenges to the person or in different conditions of the person (e.g. when the person is fatigued or alert).

The modes of operation of the apparatus 100 may differ in whether the foot sole stimulator 120 and/or the peroneal nerve stimulator 130 is active. The modes of operation of the apparatus 100 may also differ in the sensor input being used for determining triggering of generation of stimulation electrical signals.

The apparatus 100 may be configured to receive input for selecting a current mode of the apparatus 100. Additionally or alternatively, the apparatus 100 may be configured to detect a suitable mode of operation of the apparatus 100 based on input from sensors. The apparatus 100 may thus select the current mode based on received manual input and/or based on an automatically detected suitable mode. When the apparatus 100 is configured to automatically detect a suitable mode, the apparatus 100 may still receive manual input for overriding the detected suitable mode and selecting the current mode of the apparatus 100.

The control unit 110 may be configured to select the mode of operation of the apparatus 100 and control settings of the foot sole stimulator 120 and the peroneal nerve stimulator 130 accordingly. The control unit 110 may also be configured to receive the manual input for selecting the current mode.

The manual input may be received through a user interface of the apparatus 100. Thus, the apparatus 100 may e.g. comprise one or more buttons for selecting the mode of operation or the apparatus 100 may comprise a screen for providing user interaction. However, since the apparatus 100 is arranged on the leg of the person, it may be cumbersome for the person to control the apparatus 100 through direct interaction with a user interface on the carrier 102.

Alternatively, the apparatus 100 may comprise a communication unit 160 for wireless communication with a remote unit. For instance, the apparatus 100 may be configured for short-range wireless communication with a remote unit carried by the person, e.g. a smartphone. However, the communication unit 160 may alternatively be configured for long-range wireless communication enabling communication with a remote unit placed anywhere e.g. through a computer or telecommunication network.

The remote unit may execute a dedicated program, such as a dedicated phone application, for providing a user interface adapted to provide input to the apparatus 100. The manual input may be used for selecting mode of operation of the apparatus 100 but may also be used to control settings within a selected mode, such as a magnitude of the stimulation electrical signals.

The apparatus 100 may be operated in one or more of the following modes. It should also be realized that other modes of operation may be defined.

The apparatus 100 may be operated in a reflex mode, wherein the foot sole stimulator 120 is active while the peroneal nerve stimulator 130 is inactive, in a dorsiflexor mode, wherein the peroneal nerve stimulator 130 is active while the foot sole stimulator 120 is inactive, in a combined mode, wherein both the peroneal nerve stimulator 130 and the foot sole stimulator 120 are active, and in a direct mode, wherein the peroneal nerve stimulator 130 is active while the foot sole stimulator 120 is inactive and the peroneal nerve stimulator 130 is configured to provide the peroneal nerve stimulation electrical signal in dependence of the sensed muscle activity by the muscle activity sensor 150.

In the reflex mode, the apparatus 100 may stimulate activation of the nociceptive withdrawal reflex during the swing phase of gait. The nociceptive withdrawal reflex may cause a combined reflex-mediated action of hip flexion, knee flexion and ankle dorsiflexion in the person. The nociceptive withdrawal reflex is activated by stimulation of the skin under the sole of the foot.

The reflex mode may be suitable for use in the beginning of retraining of a person after e.g. a stroke, when the person has gone through the initial acute phase and is ready to start gait training. At this stage the gait is typically severely impaired, and it is of importance to use nociceptive withdrawal reflex activation to get as much movement as possible from the person and obtain gait function.

In the dorsiflexor mode, the apparatus 100 may stimulate activation of the foot dorsiflexor muscles, by direct stimulation of the peroneal nerve. The stimulation may be controlled by the one or more pressure sensors 112 located under the sole of the foot or by the inertial sensor 140. Input from the one or more pressure sensors 112 and/or the inertial sensor 140 may be used to determine the approximate time of heel lift and trigger stimulation at an appropriate time to activate foot dorsiflexion.

The dorsiflexor mode may be suitable both for training and assisting gait. In the dorsiflexor mode, sensor input may be used to detect when the person needs to dorsiflex the foot, to aid a person that is not able to perform voluntary activation of the dorsiflexor muscles. Stimulation is applied to the peroneal nerve, activating the foot dorsiflexor muscles during the swing phase. This level of activation is focused only on providing foot dorsiflexion and is to be combined with the person having some level of hip flexion and knee flexion to bring the leg forward.

In the combined mode, the apparatus 100 may provide a combination of activation of foot dorsiflexor muscles, as in the dorsiflexor mode, with activation of the nociceptive withdrawal reflex, as in the reflex mode. It may be conceivable that the magnitude of the foot stimulation electrical signal may be lower in the combined mode than in the reflex mode. The activation of the nociceptive withdrawal reflex may act as a "boost function" to further improve the aid given to the person by the stimulation of activation of foot dorsiflexor muscles. The combined mode may be suitable for use when the person gets fatigued or the surface becomes more challenging to pass for the person, such that the person may need better ground clearance compared to walking on a normal floor, such as when passing doorsteps or walking uphill or climbing stairs.

In the direct mode, the apparatus 100 may stimulate activation of the foot dorsiflexor muscles, by direct stimulation of the peroneal nerve. In contrast to the dorsiflexor mode, the stimulation may in the direct mode be controlled by a sensing of voluntary activation of peroneal nerve stimulation, which may be provided by residual or re-established muscular activity.

As in the dorsiflexor mode, the direct mode also involves stimulation of the peroneal nerve but based on input from the muscle activity sensor 150. The muscle activity sensor 150 may e.g. based on electromyography record any voluntary muscle activity that is generated by the person in the foot dorsiflexor muscles (mainly Tibialis Anterior). The muscle activity sensor 150 may further amplify the recorded voluntary muscle activity and use the recorded voluntary muscle activity as either a trigger or as direct control of the stimulation administered to the peroneal nerve. In this way, the person's own ability to activate the dorsiflexor muscles may be considered to be "amplified", giving a more natural way of performing gait and possibly improving awareness and ability of the person to activate the dorsiflexor muscles in a natural way.

According to an embodiment, other types of stimulation may be provided in combination with one or more modes of the apparatus 100. Such stimulation may provide stimulation to the brain of the person, which may be beneficial in providing neuroplasticity.

For instance, a stimulation may be provided as a rhythm which may be sensed by the person. The rhythm may aid the person to follow the rhythm when walking, which may improve gait rehabilitation and/or gait assistance. The rhythm may be provided audibly to the person, e.g. through music played to the person. However, according to an alternative, the rhythm may be provided as vibrations propagated through tissue and which may still be sensed by an ear of the person.

The control unit 110 may be configured to control output of the rhythm and to control pace of the rhythm to fit a pace of the person, such that the pace may e.g. be increased when the pace of gait is increased.

For instance, the apparatus 100 may comprise a loudspeaker arranged on the carrier 102 so as to output the rhythm. Alternatively, the apparatus 100 may comprise a vibrator arranged on the carrier 102 for providing a vibration to tissue of the person. According to yet another alternative, the rhythm may be output by an external device. Thus, the control unit 110 of the apparatus 100 may be configured to output a control signal to the external device, e.g. through wireless communication via the communication unit 160. The external device could be earpieces which may be worn by the person, so as to output the rhythm into the ears of the person. The external device could be a loudspeaker in a gait rehabilitation facility, so that the rhythm is audibly output in a room. This allows a caregiver to also hear the rhythm as the person is undergoing gait rehabilitation.

According to another embodiment, a stimulation may be provided as a light signal which may be presented to the person. Thus, a light source may project a light beam onto ground in front of the person so as to indicate to the person a target to which the foot is to be moved. The light signal may aid the person to trigger walking and may improve gait rehabilitation and/or gait assistance.

For instance, the apparatus 100 may comprise a light source arranged on the carrier 102 for outputting the light signal. For instance, the light source may be arranged at the leg of the person so as to be directed towards a position in front of a foot. However, the light source may alternatively be separately mounted on the person. For instance, the light source may be arranged at a tip of a shoe to project a light signal in front of the foot of the person.

The control unit 110 may be configured to output a control signal to the light source for controlling output of the light signal. For instance, the control unit 110 may be configured to control timing of the output of the light signal such that the light signal is shown when the person is about to take a step.

It should also be realized that the above described other types of stimulation, such as a rhythm or a light signal, may be simultaneously provided so as to provide a multitude of stimulations to the person.

The apparatus 100 may further be configured to receive input from additional sensors. For instance, the apparatus 100 may be configured to receive input from an additional inertial sensor, such as an accelerometer and/or gyroscope, that may be configured to be arranged on a healthy leg or foot of the person. The apparatus 100 may also or alternatively be configured to receive input from one or more additional pressure sensors arranged under the healthy foot of the person.

The control unit 110 may be configured to receive such additional input from additional sensors and may be configured to control operation of the apparatus 100 based on such additional input. For instance, the additional input may be useful in determining a suitable mode of operation. Also, the additional input may be useful in providing feedback of gait of the person, such that settings of the apparatus 100 may be adjusted, e.g. settings of stimulation electrical signals.

The apparatus 100 may comprise a mode detection unit 114. The mode detection unit 114 may be provided in the control unit 110.

The mode detection unit 114 may be configured to receive input from any of the sensors, such as the at least one foot pressure sensor 112, the inertial sensor 140, the muscle activity sensor 150, the additional inertial sensor arranged on the healthy leg or foot of the person, and the additional pressure sensors arranged under the healthy foot of the person. Based on this input, the mode detection unit 114 may determine whether there is a need to change the mode of operation of the apparatus 100.

For instance, the mode detection unit 114 may determine that the at least one foot pressure sensor 112 on the leg having impaired gait or on the healthy leg indicates that the leg suffering from impaired gait is never properly lifted from contact with ground. This could be used as an indication that the mode of operation may need to be switched from the dorsiflexor mode to the combined mode or the reflex mode.

According to another example, the mode detection unit 114 may determine that the inertial sensor 140 or the additional inertial sensor detects sudden stops in movement, which may be indication of the person hitting the foot into the ground and not providing sufficient clearance over ground. This could be used as an indication that the mode of operation may need to be switched from the dorsiflexor mode to the combined mode or the reflex mode.

It should be realized that the sensor input may be used in many other ways for switching mode of operation, both in direction of a need of providing more assistance to the person and in direction of a need of providing less assistance to the person (e.g. based on detecting that no problems, such as hitting foot into obstacles or not lifting the foot properly, are experienced over a period of time).

It should be realized that the apparatus 100 may be configured to switch modes of operation when external conditions or needs of the person are changing. However, according to an alternative, the apparatus 100 may be configured to switch modes of operation frequently, such as switching modes of operation at every step or every other step taken by the person. Thus, the apparatus 100 may e.g. be set to use the dorsiflexor mode and the combined mode in combination, such that each of the dorsiflexor mode and the combined mode is used every other step and the apparatus 100 constantly switches between these modes.

The apparatus 100 may further comprise a gait quality detection module 116. The gait quality detection module 116 may be provided in the control unit 110.

The gait quality detection module 116 may be configured to analyze gait quality based on sensor input. The gait quality detection module 116 may thus receive input from one or more sensors. For instance, the gait quality detection module 116 may receive input from at least one of: the at least one foot pressure sensor 112, the inertial sensor 140, the muscle activity sensor 150, the additional inertial sensor arranged on the healthy leg or foot of the person, and the additional pressure sensors arranged under the healthy foot of the person.

The gait quality detection module 116 may be configured to calculate one or more quality measures based on the sensor input. The quality measures may be used directly as an indication of gait quality or may be combined in order to determine an overall gait quality or a rating of gait quality.

For instance, the gait quality detection module 116 may be configured to determine a step length and/or stride length of the person, variations in step length and/or stride length, and trends in step length and/or stride length as a quality measure. The gait quality detection module 116 may be configured to assess an amount of pressure being asserted by the healthy leg and/or the leg suffering from impaired gait. The amount of pressure may be an indication of gait quality, as improvements in gait quality may be indicated by the person being able to assert more pressure on the leg suffering from impaired gait and less pressure on the healthy leg. Thus, amount of pressure asserted by the leg suffering from impaired gait and/or amount of pressure asserted by healthy leg may be used as a quality measure. Also or alternatively, a ratio of asserted pressures by the legs of the person may be used as a quality measure. Also or alternatively, variations in asserted pressure or ratio of asserted pressures and/or trends in asserted pressure or ratio of asserted pressures may be used as a quality measure.

The gait quality measures provided by the gait quality detection module 116 may be used as input to the mode detection unit 114. Thus, the mode detection unit 114 may automatically detect a suitable mode of operation of the apparatus 100 based e.g. on comparing gait quality measures to threshold values.

The gait quality measures may also or alternatively be communicated by the communication unit 160 to a remote unit. The remote unit may thus allow display of gait quality measures such that the person wearing the apparatus 100 may receive feedback on gait quality so as to e.g. be encouraged in gait rehabilitation and gait assistance or to enable the person to take decisions as to needs of changing mode of operation, such that manual input may be provided for changing mode of operation of the apparatus 100.

Also, the gait quality measures may be communicated by the communication unit 160 to a remote unit for providing information of gait quality to another person than the person wearing the apparatus 100. For instance, the gait quality measures may be communicated to a caregiver, allowing the caregiver to monitor trends in gait quality measures so as to enable the caregiver to give advice on gait rehabilitation and gait assistance.

Figure 2:
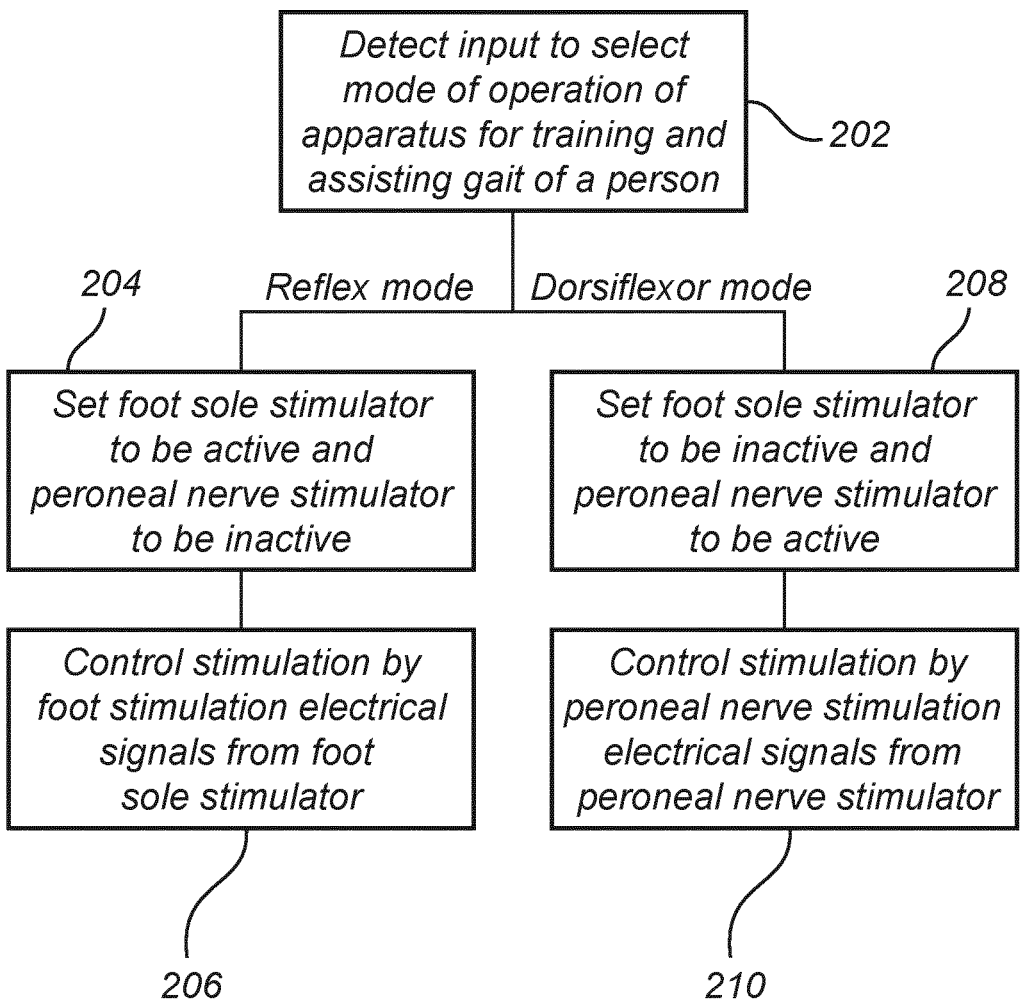
FIG. 2 is a flow chart of a method according to an embodiment.

Referring now to FIG. 2, a method for training and assisting gait of a person will be described.

The method comprises detecting 202 input to select a mode of operation of an apparatus 100 for training and assisting gait of a person. Thus, the method enables selecting mode of operation of the apparatus 100, such that versatile use of the apparatus 100 is provided and the apparatus 100 may be used in different stages of gait rehabilitation and gait assistance and may be adapted to needs of the person.

The method comprises selecting mode of operation between at least a reflex mode and a dorsiflexor mode, wherein a foot sole stimulator 120 and a peroneal nerve stimulator 130 of the apparatus 100 are selectively activated in dependence of a selected mode of operation.

In case the apparatus 100 is selected to be operated in the reflex mode, the method comprises setting 204 the foot sole stimulator 120 to be active and the peroneal nerve stimulator 130 to be inactive, and based on input from one or more sensors 112, 140, 150 sensing input related to movement of the foot of the person, controlling 206 stimulation by foot stimulation electrical signals from the foot sole stimulator 120 to the foot sole of the person for stimulating a nociceptive withdrawal reflex during gait of the person.

In case the apparatus 100 is selected to be operated in the dorsiflexor mode, the method comprise setting 206 the foot sole stimulator 120 to be inactive and the peroneal nerve stimulator 130 to be active, and based on input from one or more sensors 112, 140, 150 sensing input related to movement of the foot of the person, controlling 208 stimulation by peroneal nerve stimulation electrical signals from the peroneal nerve stimulator 130 to the peroneal nerve of the person for stimulating activation of foot dorsiflexor muscle.

The method may further comprise selecting mode of operation between further modes, such as a combined mode, wherein both the foot sole stimulator 120 and the peroneal nerve stimulator 130 are active, and a direct mode, wherein the peroneal nerve stimulator 130 is active and the foot sole stimulator is inactive and stimulation by peroneal nerve stimulation electrical signals is controlled based on a muscle activity sensor 150 for sensing muscle activity in the leg of the person.

The method may further comprise receiving sensor input providing feedback of the gait of the person. For instance, the sensor input may be used for determining measures relating to gait quality.

The method may further comprise selecting a mode of operation of the apparatus 100 based on the feedback from sensor input.

The method may be performed by a processing unit that executes a computer program, which may comprise computer-readable instructions for causing the processing unit to perform the method.

The processing unit performing the method may be arranged in the apparatus 100, but the processing unit performing the method may alternatively be arranged in a remote unit communicating control signals to the apparatus 100.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For instance, the control unit 110 is described above as being arranged on the carrier 102, and the control unit 110 is described as potentially having several different functionalities. However, it should be realized that the above-described functionality or at least part of the above-described functionality of the control unit 110 may alternatively be provided in a remote unit. This implies that the apparatus 100 may not need as much processing power, which may save battery life of the apparatus 100. In particular, functionalities of the control unit 110 which may require processing power, and which are not very critical to be performed in real-time may be provided by the remote unit based on communication of sensor input to the remote unit. For instance, the mode detection unit and the gait quality detection module may be arranged in the remote unit.

The invention claimed is:

1. An apparatus for training and assisting gait of a person, said apparatus comprising:

a sensor configured for being arranged in relation to a foot or leg of the person for sensing input related to movement of the foot of the person;

a foot sole stimulator for providing a foot stimulation electrical signal to the foot sole of the person for stimulating a nociceptive withdrawal reflex;

a peroneal nerve stimulator for providing a peroneal nerve stimulation electrical signal to the peroneal nerve of the person for stimulating activation of foot dorsiflexor muscle;

wherein at least the foot sole stimulator is configured to provide the foot stimulation electrical signal in dependence of the input sensed by the sensor;

wherein the apparatus is configured to be operated in at least two different modes for selectively activating at least one of the foot sole stimulator or the peroneal nerve stimulator; and wherein the apparatus is configured to be operated in a reflex mode, wherein the foot sole stimulator is active while the peroneal nerve stimulator is inactive, and in a dorsiflexor mode, wherein the peroneal nerve stimulator is active while the foot sole stimulator is inactive and in a combined mode, wherein both the peroneal nerve stimulator and the foot sole stimulator are active.

2. The apparatus according to claim 1, wherein the sensor comprises a foot pressure sensor configured for being arranged beneath a foot of the person for sensing a pressure asserted by the foot of the person, wherein the foot sole stimulator and/or the peroneal nerve stimulator are configured to provide the foot stimulation electrical signal and the peroneal nerve stimulation electrical signal, respectively, in dependence of the sensed pressure by the foot pressure sensor.

3. The apparatus according to claim 1, further comprising an inertial sensor configured for being arranged on or beneath the foot of the person or on a leg of the person for sensing a movement of the foot and/or leg of the person, wherein the foot sole stimulator and/or the peroneal nerve stimulator are configured to provide the foot stimulation electrical signal and the peroneal nerve stimulation signal, respectively, in dependence of a sensed movement by the inertial sensor.

4. The apparatus according to claim 1, further comprising a muscle activity sensor configured for being arranged on a leg of the person for sensing muscle activity in the leg of the person, wherein the apparatus is further configured to be operated in a direct mode, wherein the peroneal nerve stimulator is configured to provide the peroneal nerve stimulation electrical signal in dependence of the sensed muscle activity by the muscle activity sensor.

5. The apparatus according to claim 1, further comprising a control unit for controlling the apparatus to be operated in a selected mode.

6. The apparatus according to claim 5, wherein the control unit is configured to receive manual input for selecting a current mode of the apparatus.

7. The apparatus according to claim 5, wherein the control unit further comprises a mode detection unit, which is configured to use input from the sensor for sensing input related to movement of the foot of the person to automatically detect a suitable mode of operation of the apparatus for selecting a current mode of the apparatus.

8. The apparatus according to claim 5, wherein the control unit is configured to receive input from additional sensors, such as an additional inertial sensor configured to be arranged on a healthy leg of the person, for controlling operation of the apparatus and/or providing feedback of gait of the person.

9. The apparatus according to claim 5, wherein the control unit further comprises a gait quality detection module for analyzing gait quality based on sensor input.

10. The apparatus according to claim 5, further comprising a carrier being configured to be arranged beneath the foot of the person and along at least a lower leg of the person, wherein the sensor for sensing input related to movement of the foot of the person, the foot sole stimulator, the peroneal nerve stimulator and the control unit 10 are mounted in or on the carrier.

11. The apparatus according to claim 1, wherein the foot sole stimulator comprises at least one foot electrode configured to be arranged in contact with a foot sole of the person and a pulse generator for generating the foot stimulation electrical signal, and wherein the peroneal nerve stimulator comprises at least one leg electrode configured to be arranged in contact with a leg of the person for providing the peroneal nerve stimulation electrical signal to the peroneal nerve and a pulse generator for generating the peroneal nerve stimulation electrical signal, wherein the pulse generator of the foot sole stimulator and the pulse generator of the peroneal nerve stimulator may optionally be shared.

12. A method for training and assisting gait of a person, said method comprising:

detecting input to select a mode of operation of an apparatus for training and assisting gait of a person between at least a reflex mode and a dorsiflexor mode, wherein a foot sole stimulator and a peroneal nerve stimulator of the apparatus are selectively activated in dependence of a selected mode of operation;

in case the apparatus is selected to be operated in the reflex mode:

setting the foot sole stimulator to be active and the peroneal nerve stimulator to be inactive; and based on input from a sensor sensing input related to movement of the foot of the person, controlling stimulation by foot sole stimulation electrical signals from the foot sole stimulator to the foot sole of the person for stimulating a nociceptive withdrawal reflex during gait of the person;

in case the apparatus is selected to be operated in the dorsiflexor mode:

setting the foot sole stimulator to be inactive and the peroneal nerve stimulator to be active; and based on input from a sensor sensing input related to movement of the foot of the person, controlling stimulation by peroneal nerve stimulation electrical signals from the peroneal nerve stimulator to the peroneal nerve of the person for stimulating activation of foot dorsiflexor muscle; and in case the apparatus is selected to be operated in a combined mode, setting the foot sole stimulator to be active and the peroneal nerve stimulator to be active; and based on input from a sensor sensing input related to movement of the foot of the person, controlling stimulation by foot sole stimulation electrical signals from the foot sole stimulator to the foot sole of the person for stimulating a nociceptive withdrawal reflex during gait of the person and controlling stimulation by peroneal nerve stimulation electrical signals from the peroneal nerve stimulator to the peroneal nerve of the person for stimulating activation of foot dorsiflexor muscle.

13. The method according to claim 12, further comprising receiving sensor input relating to gait quality and analyzing gait quality based on the sensor input, wherein the gait quality may be used as input to select a mode of operation of the apparatus.

14. A computer program product comprising computer-readable instructions such that when executed on a processing unit the computer-readable instructions will cause the processing unit to perform the method according to claim 12.

* * * * *